United States Patent
Brinster et al.

(10) Patent No.: US 6,365,104 B1
(45) Date of Patent: Apr. 2, 2002

(54) ASSEMBLY FOR ANALYZING BLOOD SAMPLES

(75) Inventors: Wayne L. Brinster, Kinnelon, NJ (US); Stephen C. Wardlaw, Lyme; Robert A. Levine, Guilford, both of CT (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/344,990

(22) Filed: Jun. 25, 1999

(51) Int. Cl.$^7$ .............................................. G01N 21/00
(52) U.S. Cl. .............................. 422/58; 422/73; 422/99; 422/102; 436/69; 436/70; 436/174; 436/177
(58) Field of Search ........................... 422/68.1, 73, 99, 422/100, 101, 102, 913, 916, 918, 58; 436/66, 69, 70, 174, 180, 177; 356/39–41

(56) References Cited

U.S. PATENT DOCUMENTS

| | | | |
|---|---|---|---|
| 4,639,242 A | * | 1/1987 | Babson .......................... 494/37 |
| 4,652,429 A | * | 3/1987 | Konrad ......................... 422/102 |
| 5,506,145 A | * | 4/1996 | Bull et al. ...................... 436/69 |
| 5,632,905 A | * | 5/1997 | Haynes ......................... 210/782 |
| 5,690,242 A | * | 11/1997 | Campbell, Jr. ............... 215/273 |
| 5,736,033 A | * | 4/1998 | Coleman et al. ............. 210/122 |
| 5,811,303 A | * | 9/1998 | Ryan ............................. 436/16 |
| 5,834,217 A | * | 11/1998 | Levine et al. ............... 435/7.24 |

* cited by examiner

Primary Examiner—Jill Warden
Assistant Examiner—Dwayne K Handy
(74) Attorney, Agent, or Firm—William W. Jones

(57) ABSTRACT

An improved system can be used to examine a centrifuged sample of anticoagulated whole blood for evidence of blood borne rare events such as: circulating cancer cells; malarial parasites; other hemato-parasites; bacteria; and the like; and can also be used in the measurement of hematocrit and hemoglobin, as well as white cell and platelet count values in the centrifuged blood sample. The system includes a transparent blood sample tube and an insert that is placed in the tube. The insert floats on the packed erythrocyte layer in the centrifuged blood sample, and expands all of the layers above the packed erythrocyte layer. The insert also forces any blood borne rare events to the periphery of the blood sample in the tube where such events can be detected through the tube wall. The bottom end of the tube is closed by a closure which includes an outer sheath and an inner plug that projects up into the tube bore to a degree necessary to elevate at least the upper portion of the packed erythrocyte layer into which the insert has settled sufficiently so as to be detectable above the cap, and preferably examinable microscopically after the blood sample has been centrifuged. The outer sheath of the tube closure includes an outer annular surface which is provided with sensible indicia. The indicia are operable to enable an instrument or a person examining the sample to rotate the tube, and to determine the circumferential location in the tube of any suspicious objects noted in the blood sample.

5 Claims, 2 Drawing Sheets

ASSEMBLY FOR ANALYZING BLOOD SAMPLES

TECHNICAL FIELD

This invention relates to the analysis of centrifuged anticoagulated blood samples which are contained in a centrifuge tube having a blood constituent-elongating insert therein. More particularly, this invention relates to a centrifuge tube assembly which is useful for measuring various blood parameters such as hematocrit, and which is also designed to examine the blood sample for evidence of rare events such as: blood-borne cancer cells; malarial parasites; other hemato-parasites; bacteria; or the like. The blood sample can also be analyzed in the tube for hematocrit and hemoglobin values as well as white cell and platelet counts.

BACKGROUND OF THE INVENTION

U.S. Pat. No. 4,027,660 granted to Stephen C. Wardlaw et al describes a method and paraphernalia for use in measuring differential white cell and platelet counts in a centrifuged sample of anticoagulated whole blood. The procedure described in this patent suggests that a scale be used to measure the length of physically expanded white cell and platelet layers, and that a table be used to convert the measured layer lengths to definitive blood cell and platelet layer counts. U.S. Pat. Nos. 4,156,570 and 4,558,947 granted to Stephen C. Wardlaw disclose instruments which are used to measure cell and platelet counts in centrifugal blood samples contained in the aforesaid tube-insert paraphernalia, which instruments include microprocessor controllers that are programmed to automatically convert measured erythrocyte and platelet layer band lengths into cell and platelet counts. U.S. Pat. No. 4,259,012 granted to Stephen C. Wardlaw, and U.S. Pat. No. 5,132,087 granted to Kristen L. Manion et al describe devices for measuring white cell, platelet and hematocrit counts, which devices do not require conversion tables or microprocessor controllers. U.S. Pat. No. 4,209,226 granted to Stephen C. Wardlaw et al describes an optical viewing instrument which includes a capillary tube and a holder which includes a slot for containing the capillary tube. U.S. Pat. No. 4,190,328 granted to Robert A. Levine et al describes a process for the detection of blood-borne parasites wherein a centrifuge tube with an insert are used to trap blood-borne parasites between the tube and the insert so that the parasites will be visible under magnification through the tube.

The aforesaid group of patents all relate to inventions which utilize a tube and insert combination to either measure blood sample parameters quantitatively; or detect the presence or absence of blood-borne parasites, such as malarial parasites, microfilaria, or the like. In the latter case, the blood samples in the tubes are examined immersed in oil and under magnification, typically with an epi-illuminating UV or fluorescence microscope such as described in U.S. Pat. No. 5,198,927, granted Mar. 30, 1993 to R. R. Rathbone et al; and U.S. Pat. No. 5,349,468, granted Sep. 20, 1994 to R. R. Rathbone et al. When the centrifuged blood sample is being analyzed for parasites, or for blood borne rare events, there is currently no way to positively ascertain the location of the evidence of rare events in the centrifuge tube. The reason for this fact is that analysis of the blood sample in the tubes requires that the tubes be rotated so that the blood layers trapped between the tube wall and the insert can be thoroughly examined throughout the entire three hundred sixty degree circumference of the tube.

Present closures of capillary tubes are of three different varieties: simple clay, which is pressed into the tube from a tray; an internal closure described in U.S. Pat. No. 5,325,977 granted Jul. 5, 1994 to J. L. Haynes et al; and caps of the type shown in U.S. Pat. No. 5,132,087, granted Jul. 21, 1992 to K. L. Manion et al, and also shown in other issued patents.

To accurately measure the hematocrit height one must be able to accurately locate the lower and upper end of the packed erythrocyte layer. To examine centrifuged samples of blood for rare events, one must be able to position the objective of a microscope proximate the tube. The degree of sample magnification needed to examine the sample for rare events is generally 50×. Microscopic examination of the sample generally requires the use of an oil immersion for the tube on the microscope stage, and an objective lens which has a working distance of at least one hundred sixty microns. During the sample examination, the objective lens of the microscope must be disposed closely adjacent to the surface of the tube, or even touching the tube through the oil layer.

During microscopic examination of the sample, the tube must be manually rotated about its axis using one's fingers so as to be able to examine the entire circumference of the tube in the areas of interest. The areas in the blood sample which are of interest for rare events can include the areas in the blood sample which surround the portions of the insert which are submerged in the erythrocyte layer, and which are surrounded by both erythrocytes, buffy coat components, and, in some ases, by plasma at the upper end of the insert.

Closures of the aforesaid first and second types, while permitting accurate detection of the lower and upper ends of the erythrocyte layer, and permitting the the oil-immersed microscope objective to contact the capillary tube, do not facilitate accurate rotation of the oily tube and closure. The reason for this is that the glass tube and closure are smooth, and are frequently covered with oil thereby rendering the tube assembly extremely difficult to rotate when rotational pressure is manually applied with one's fingers. Furthermore, if manual pressure is applied to the tube assembly, the tube might fracture, thereby destroying the sample and potentially injuring the technician.

Closure caps of the third type described above, while not impeding manual rotation of the tube by means of manual contact with the cap, do render detection of the lower end of the erythrocytes difficult because the lower end of the erythrocyte layer will be obscured by such closure caps. A person with severe anemia, or one experiencing abdominal bleeding, can have a hematocrit of about twenty or less. In cases of such low hematocrits, i.e., hematocrits which are below levels of about twenty, the upper end of the packed erythrocytes may be positioned at or near at the upper edge of the cap, thereby rendering the upper end of the packed erythrocyte layer difficult to detect and obscured by the closure cap. Thus, when using closure caps of the aforesaid third type, hematocrit measurement may be difficult, or impossible to perform.

When microscopical rare event examination is attempted of the centrifuged blood sample in a tube-and-insert assembly that utilizes the aforesaid third type of closure, one may be unable to position the objective lens set of the microscope sufficiently close to the sample tube to examine appropriate portions of the centrifuged sample due to mechanical interference between the microscope's objective lens set and the tube assembly closure cap. Thus, in all centrifuged blood samples which are contained in an assembly that employs the aforesaid third type of closure cap, at least a portion of the expanded portion of the erythrocyte layer which surrounds the float cannot be examined under a microscope for rare events, and in a blood sample with a hematocrit of less than about twenty, none of the expanded portion of the erythrocyte layer which surrounds the float can be examined under a microscope for rare events. Thus, while the third type of closure cap may allow manual rotation of an oily sample tube assembly, such a sample tube assembly limits the ability to microscopally examine the expanded portion of the erythrocyte layer which surrounds the float for the presence or absence of rare events.

The problem which is encountered in the examination of the blood samples for hematocrit relates to the fact that the closures of the third type entrap a significant portion of the erythrocytes, thereby lowering the upper end of the erythrocyte layer, and obscuring the entrapped erythrocytes from a hematocrit scale or optical sensors. This problem prevents hematocrits of less than about twenty from being accurately measured. It will be noted that the hematocrit scale shown in the aforesaid U.S. Pat. No. 5,132,087 patent only goes down to twenty. Thus, critical hematocrit values are not readable with this prior art equipment.

It would be desirable to be able to examine a centrifuged anticoagulated whole blood sample for evidence of blood borne rare events, such as circulating cancer cells, malarial parasites, microfilaria, bacteria, and the like, with equipment which allows the investigator to microscopally examine essentially the entire erythrocyte column for evidence of rare events, and accurately record the location of any noted rare event evidence in the sample holder; and also obtain accurate hematocrit, hemoglobin, and blood constituent count values from the blood sample in the same sample tube.

DISCLOSURE OF THE INVENTION

This invention relates to a system which can be used to examine a centrifuged sample of anticoagulated whole blood for rare events, microfilaria, and can also be used in the measurement of hematocrit values in the centrifuged blood sample. The system of this invention includes a transparent sample tube, which may be a capillary tube, an insert which resides in the tube in the manner described in the above-identified prior patents. The insert floats in the packed erythrocyte layer in the centrifuged blood sample, and vertically or longitudinally expands all of the cell layers which surround the insert or float. The insert also forces any evidence of rare events to the periphery of the blood sample in the tube where it can be detected through the tube wall.

The bottom end of the tube is closed by means of a cap which includes an inner plug that extends up into the tube bore to an extent necessary to ensure that the entire centrifuged erythrocyte layer will be visible in the tube above the cap when the blood sample is centrifuged. The tube closure cap also includes an outer tube-engaging sheath having annular surface which is provided with differentiated sensible indicia, such as numbers or letters, or the like. The indicia can be embossed or debossed, or otherwise placed on the surface of the closure cap, and are evenly spaced about the annular surface so that one examining the sample can determine the circumferential location in the tube of any suspicious objects noted in the blood sample. The microscope stage can also be equipped with an axial movement-measuring micrometer so that the axial position in the tube of any rare event evidence noted in the blood sample can also be determined and recorded. The assembly can thus be used to enable the determination of both the axial and circumferential coordinates of each piece of rare event evidence noted in the blood sample. The indicia, when raised on the annular surface, impart increased friction to the closure cap so that the tube can be more easily manually rotated on a microscope slide despite the tube assembly's tube and cap being slippery as a result of being immersed in oil.

The outer sheath of the closure cap could, instead or additionally, be provided with molded gear teeth which would include a sensible reference tooth, or other sensible structure, that would enable the tube to be manually or mechanically rotated from the same start point each time the tube is inserted into a reading instrument. A complementary rotating gear could be provided in the reading instrument, which rotating gear can be controlled by an instrument controller processor, or the rotating gear could be manually-actuated. Thus, the closure cap with its raised indicia and/or molded gear teeth will enable one to visually record the location of rare event evidence, or to instrumentally record the location of any rare event evidence found in the blood sample, and would also allow one to selectively rotate the tube to a new field of view which is to be inspected.

It is therefore an object of this invention to provide an improved assembly for examining a sample of centrifuged anticoagulated blood for blood borne evidence of physiological rare events.

It is a further object of this invention to provide an assembly of the character described which includes a transparent sample tube containing a volume-occupying insert and having a basal closure cap.

It is an additional object of this invention to provide an assembly of the character described wherein the closure cap is provided with an internal plug which extends into the tube and provides a surface for centrifuged erythrocytes to settle onto to a degree wherein virtually the entire erythrocyte layer will be visible through the tube.

It is yet an additional object of this invention to provide an assembly of the character described wherein the internal plug extends into the tube sufficiently so as to locate the lowest end of the erythrocyte layer in a position within the tube that is sufficiently offset from the remainder of the closure cap so that the objective lens set of a microscope can be positioned relative to the tube so that the microscope can be focused on the portion of the erythrocyte layer which surrounds the insert in the tube.

It is another object of this invention to provide an assembly of the character described wherein the closure cap is provided with an external annular sheath having an outer surface that has differentiated sensible indicia thereon for the purpose of identifying the rotational position of the tube and sample.

It is yet another object of this invention to provide an assembly of the character described wherein the external annular sheath has an outer surface that is roughened for the purpose of facilitating rotation of the tube and sample while the tube is positioned in an examining instrument.

These and other objects and advantages of the invention will become more readily apparent from the following detailed description of several embodiments of the invention when taken in conjunction with the accompanying drawings in which:

DETAILED DESCRIPTION OF SPECIFIC EMBODIMENTS OF THE INVENTION

Figure 1:
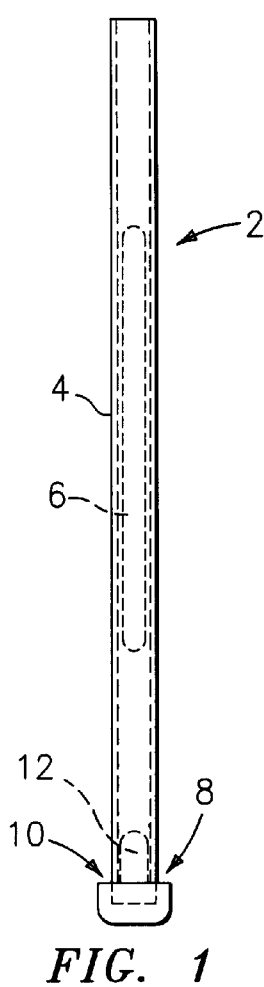
FIG. 1 is a side elevational view of a centrifuge tube assembly formed in accordance with this invention.

Referring now to the drawings, there is shown in FIG. 1 a centrifuge tube assembly denoted generally by the numeral 2. The assembly 2 includes a transparent sample-containing tube 4 in which an insert 6 is disposed. The basal end 8 of the tube 4 is closed by a closure cap 10 after the tube 4 has been filled with the anticoagulated blood sample. As noted above, the tube 4 can be a capillary tube so that the blood sample can be introduced into the tube 4 from a finger stick or from a sample of blood drawn from a larger blood harvesting tube, such as a "Vacutainer" ® tube sold by Becton Dickinson and Company of Franklin Lakes, N.J.

Figure 2:
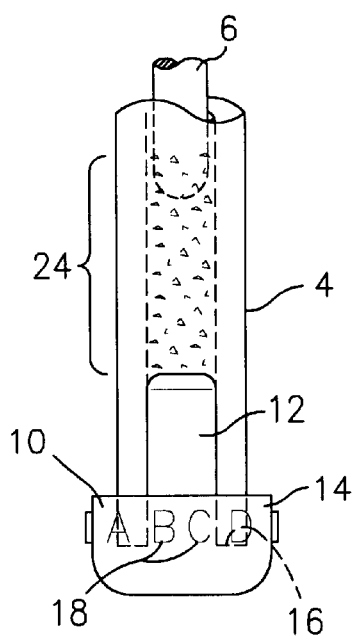
FIG. 2 is a side elevational view of the closure cap of the assembly of FIG. 1.
Figure 3:
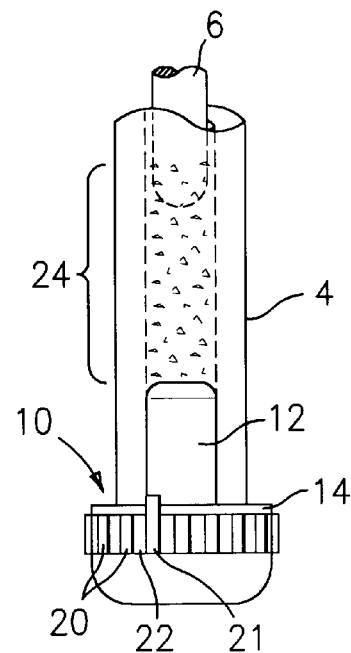
FIG. 3 is a side elevational view similar to FIG. 2, but showing an alternative embodiment of the closure cap.

The closure cap 10, as noted in FIG. 2, includes a central plug 12 and an outer part having an annular surface 14. A medial annular recess 16 in the closure cap 10 receives the basal end 8 of the tube 4. The annular surface 14 bears sensible differentiated indicia 18, which in the embodiment shown in FIG. 2 are letters of the alphabet. These indicia 18 are preferably circumferentially separated from each other by known intervening angles, so that the angular location of suspicious material found in the blood sample in the tube 4 will be known. The ability to determine the angular location of any suspicious material found in the blood sample allows one to circumferentially re-locate such suspicious materials for a more precise analysis, or for removal from the blood sample. When the sample is examined with a microscope, the stage of the microscope can be provided with a vernier scale so as to be able to determine the longitudinal position of the suspicious material within the tube 4. Thus circumferential and longitudinal coordinates can be established for each event detected. The plug 12 provides a surface which is clearly detectable through the tube 4, and onto which the packed erythrocyte layer will settle, so as to facilitate accurate measurements of hematocrit values in the centrifuged blood samples. As seen in FIG. 3, the outer surface 14 of the cap 10 may be provided with gear teeth 20 which will allow the tube assembly 2 to be automatically rotated in an automatically operated instrument. The gear teeth will include a unique tooth or valley 22 which can be detected by the analyzing instrument so as to establish a starting point for the rotation of the tube assembly 2. The instrument will scan the tube longitudinally, rotate the tube, scan it again longitudinally, rotate it again, and so forth. The instrument will be operated by a processor that can record both the rotational and longitudinal positions of the tube assembly 2 when any suspicious events are sensed in the blood sample.

Figure 4:
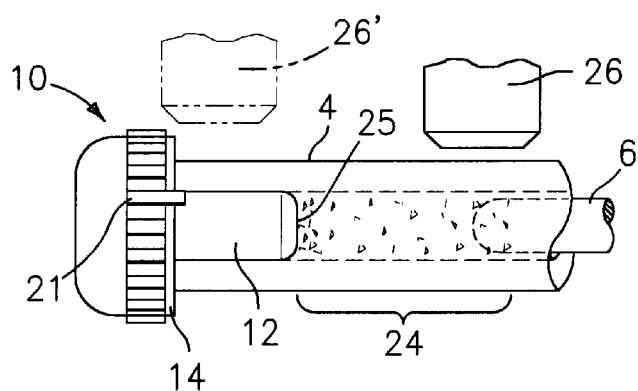
FIG. 4 is a fragmented side elevational view of the closed end of the tube assembly showing how a microscope objective lens can approach the tube to inspect its contents.

FIG. 4 illustrates how the improved closure cap 10 elevates the entire erythrocyte layer 24 in the tube 4, and spaces the bottom 25 of the layer 24 away from the outer cap surface 14 so that the objective lens housing 26 can be brought sufficiently close to the tube 4 to allow microscopic examination of the contents of the periphery of the erythrocyte layer 24. When the prior art cap configuration is used, the location of the inner surface which supports the erythrocyte layer 24 will be in the plane 11 which is indicated in phantom lines in FIG. 4. As previously noted, in such a case, the outer cap surface 14 obscures at least a part of the erythrocyte layer 24. The outer cap surface 14 also prevents the objective lens housing 26 (shown in phantom lines) from being positioned close enough to the tube 4 to examine even a portion of the erythrocyte layer 24 that is not obscured by the cap surface 14, and as noted, the obscured portion of the erythrocyte layer 24 also cannot be examined by the microscope. Thus, in samples with low hematocrits, it is possible that none of the erythrocyte layer 24 could be microscopically examined using the prior art closure caps.

Figure 5:
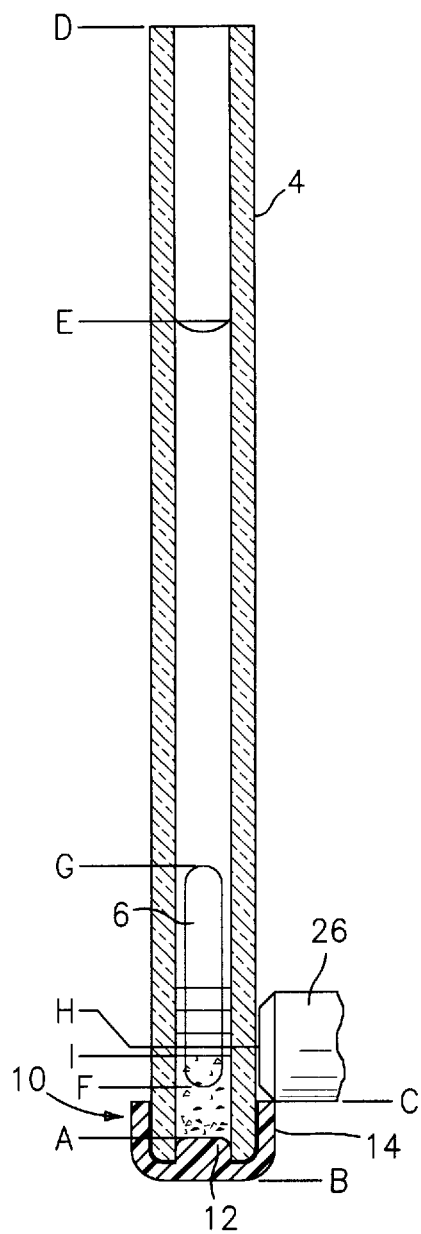
FIG. 5 is a side elevational view of a sampling tube assembly formed in accordance with the prior art which shows the obscuring of erythrocytes by a prior art closure cap and shows typical dimensions of the various portions of the prior art sample tube assembly.
Figure 6:
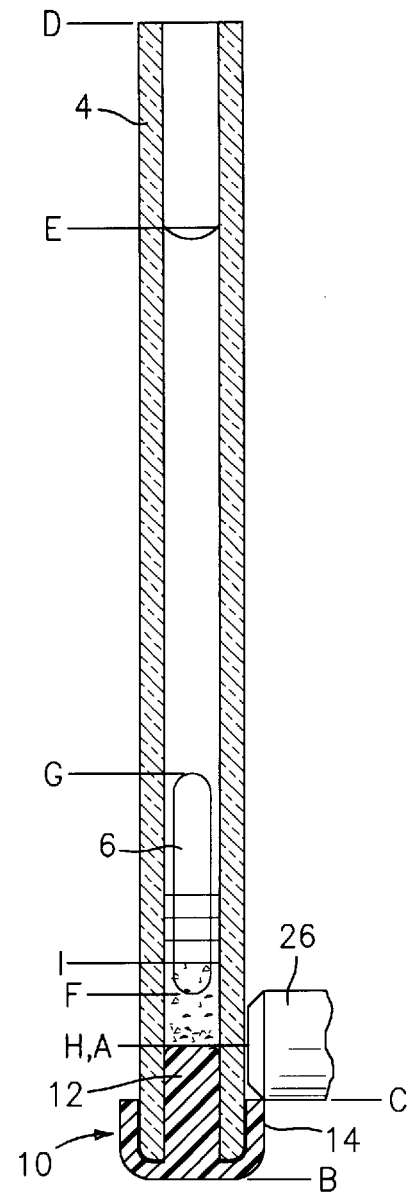
FIG. 6 is a side elevational view of a sampling tube assembly formed in accordance with this invention which shows the lack of obscuring of erythrocytes by the closure cap of this invention and shows typical dimensions of the various portions of the sample tube, as in FIG. 5.

FIGS. 5 and 6 show the location of various key components of the sampling assembly and the centrifuged blood sample when the latter is a sample having a hematocrit of about twenty, or less. FIG. 5 shows the low hematocrit blood sample contained in a prior art blood sampling assembly, and FIG. 6 shows the low hematocrit blood sample contained in a blood sampling assembly formed in accordance with this invention.

In both FIGS. 5 and 6, "A" designates the upper surface of the closure cap plug 12 and also the lower end of the centrifuged erythrocyte pack; "B" designates the lower surface of the closure cap 10; "C" designates the upper edge of the closure cap's outer surface 14; "D" designates the upper end of the tube 4; "E" designates the upper miniscus of the centrifuged blood sample in the tube 4; "F" designates the lower end of the insert 6; "G" designates the upper end of the insert 6; "H" designates the axis of the microscope objective lens 26; and "I" designates the upper end of the centrifuged erythrocyte pack in the tube 4.

When a capillary tube and float assembly of the type presently used for the diagnosis of malaria (QBC® malaria tube, Catalog No. JO-053005, Becton Dickinson and Company, Franklin Lakes, N.J.), which is seventy five mm long, and which contains 0.3 mg potassium oxalate, 5.6 μgm acridine orange, 3.8 USP units of sodium heparin, and 0.44 mg $K_2EDTA$, is used as the sampling tube 4 for a blood sample having a hematocrit below about 39, problems begin to be encountered with the examination of the blood sample for malarial or other rare event evidence in the key area of the blood sample. The key area to be examined for rare event detection is the area between F and I, and in certain cases between F and G. in FIGS. 5 and 6. In order for a conventional microscopic examination of this entire area, the distance between C and F must be at least 6 mm, which is equal to one half of the diameter of the portion of the microscope's objective lens set which must be positioned in close proximity, or in abutment with the exterior of the sample tube 4, so as to allow F and H to be aligned. We have found that with hematocrits of about 39 (38.8), the distance between C and F is 5 mm whereby the entire sample area between F and G may not be able to be microscopally examined. With a hematocrit of about 27 (26.5), the distance between C and F is only 2 mm. With a hematocrit of about 23 (23.1), the distance between C and F is only 1.5 mm. Finally, with a hematocrit of about 19 (18.6), the distance between C and F is only 0.5 mm. All of the aforesaid dimensions occur when the prior art sample tube assembly shown in FIG. 5 is used to analyze the blood sample. Thus when the prior art sample tube assembly is used to analyze blood samples having lower, but frequently occurring, hematocrits, the detection of rare events in the blood sample is impeded, and in extreme cases, disabled.

When the embodiment of the invention shown in FIG. 6 is used to assay the same low hematocrit blood samples, the lower end A of the erythrocyte cell pack is elevated by the upper surface of the closure cap plug 12 so that, preferably, the entire packed erythrocyte layer is positioned above the lens axis H, and at least the level F is positioned evenly with the lens axis H. Thus, with the embodiment of the invention shown in FIG. 6, the entire area FG of the blood sample can be examined for rare events by the lens 26. It will be appreciated that the closure cap plug 12 must elevate the lower end of the erythrocyte layer A sufficiently to enable the lens 26 to scan the area FI for rare events if the assembly is to be useful for rare event detection; and that it is also desirable for the closure cap plug 12 to elevate the erythrocyte layer as shown in FIG. 6 so that the entire erythrocyte and white cell layers can be examined by the lens 26. The assembly should be dimensioned so that a blood sample having a hematocrit of as low as 8–10% of the total blood sample can be examined for rare events.

The assembly 2 is used in the following manner. The blood sampling tube 4 is filled with blood, and the insert 6 is placed in the tube 4. The basal end 8 of the tube 4 is sealed with the closure 10, and the filled assembly 2 is placed in a centrifuge and centrifuged for a period of time sufficient to fully compact the various cell layers in the blood sample and to cause the insert 6 to settle onto the packed erythrocyte layer. The centrifuged blood sample is then examined under magnification visually so as to determine whether there is any evidence of rare events in the blood sample. The angular and longitudinal location of any suspicious materials found in the blood sample in the tube 4 is noted. The blood sample can then be visually or optically examined to measure the hematocrit in the centrifuged sample. The blood sample can also be used to determine both white cell and platelet counts and hemoglobin, as described in the prior art. Once the angular and longitudinal locations of any suspicious materials in the blood sample have been identified, the contents of the sample tube can be more thoroughly examined so as to determine the apparent nature or origin of the aforesaid materials.

It will be readily appreciated that the use of the apparatus of this invention will allow the identification of the circumferential and longitudinal location of any suspicious materials noted in the centrifuged blood sample in the tube, so that such suspicious materials can be re-located in the sample and further analyzed. The sample in the tube can be examined throughout its entire extent, and no rare event-containing part of the sample is obscured by the sample tube assembly components. The apparatus of this invention will also allow an accurate determination of hematocrit, hemoglobin, white cell counts and platelet counts in a centrifuged blood sample contained in the sample tube, as described in the prior art.

Since many changes and variations of the disclosed embodiments of the invention may be made without departing from the inventive concept, it is not intended to limit the invention otherwise than as required by the appended claims.

What is claimed is:

1. An assembly for detecting the presence or absence of rare events in a sample of centrifuged anticoagulated whole blood which assembly is postioned on a microscopal instrument, said assembly comprising:

a) a transparent blood sample tube;

b) an insert in said blood sample tube, which insert is operative to create a volumetrically restricted zone in said sample tube, which volumetrically restricted zone will be partially occupied by low density erythrocytes contained in the centrifuged blood sample;

b) a closure for sealing one end of said tube, said closure including an inner plug portion which extends into a bore in said tube, and an outer sheath portion which fits tightly about an outer surface of said tube; and c) said outer sheath portion including means for identifying an extant rotational position of said tube relative to the microscopal instrument.

2. The assembly of claim 1 wherein said means for identifying includes visually indentifiable indicia.

3. The assembly of claim 2 wherein said visually indentifiable indicia are molded into said outer sheath portion.

4. The assembly of claim 1 wherein said means for identifying includes mechanically identifiable mechanisms molded into said outer sheath portion.

5. The assembly of claim 4 wherein said mechanically identifiable mechanisms are gear teeth and wherein said gear teeth include at least one unique tooth or valley which can be detected so as to establish a starting point for rotation of the assembly.

\* \* \* \* \*